US007303610B2

(12) United States Patent
Zilioli et al.

(10) Patent No.: US 7,303,610 B2
(45) Date of Patent: Dec. 4, 2007

(54) CHROMATOGRAPHY COLUMN ASSEMBLY

(75) Inventors: Giacinto Zilioli, Cernusco Sul Naviglio (IT); Riccardo Facchetti, Lecco (IT); Paolo Magni, Besana in Brianza (IT)

(73) Assignee: Thermo Electron S.p.A., Rodano (MI) (IT)

( * ) Notice: Subject to any disclaimer, the term of this patent is extended or adjusted under 35 U.S.C. 154(b) by 255 days.

(21) Appl. No.: 10/517,199

(22) PCT Filed: Oct. 22, 2003

(86) PCT No.: PCT/IB03/04904

§ 371 (c)(1),
(2), (4) Date: Dec. 8, 2004

(87) PCT Pub. No.: WO2004/040294

PCT Pub. Date: May 13, 2004

(65) Prior Publication Data

US 2005/0189298 A1 Sep. 1, 2005

(30) Foreign Application Priority Data

Oct. 30, 2002 (IT) .......................... MI2002A2310

(51) Int. Cl.
   *B01D 53/02* (2006.01)
(52) U.S. Cl. .............................. 96/101; 96/102; 95/87; 73/23.39

(58) Field of Classification Search .................. 96/101, 96/102, 103, 104; 422/70, 89, 90; 95/82, 95/83, 84, 87, 88; 73/23.35, 23.39; 210/656, 210/198.2
See application file for complete search history.

(56) References Cited

U.S. PATENT DOCUMENTS

| 4,726,822 A | * | 2/1988 | Cates et al. .................... 96/101 |
| 5,589,630 A | | 12/1996 | Wiegand et al. |
| 5,808,178 A | * | 9/1998 | Rounbehler et al. ........ 73/23.39 |
| 6,209,386 B1 | * | 4/2001 | Mustacich et al. .......... 73/23.39 |

FOREIGN PATENT DOCUMENTS

| EP | 0 310 867 | | 9/1988 |
| WO | WO 02/40988 A1 | * | 5/2002 |

* cited by examiner

*Primary Examiner*—Duane Smith
*Assistant Examiner*—Robert A Clemente
(74) *Attorney, Agent, or Firm*—Nixon & Vanderhye P.C.

(57) ABSTRACT

Chromatography column assembly of the direct heating type, comprising at least a capillary column, at least a tubular structure which envelops the capillary column and is coaxial with it, means to directly heat the column, means to detect the temperature of the column and one or more electrically insulating covering elements, wherein the tubular structure comprises a plurality of tubular meshes each formed of a plurality of filaments woven together (FIG. 3).

22 Claims, 2 Drawing Sheets

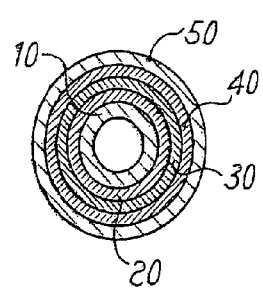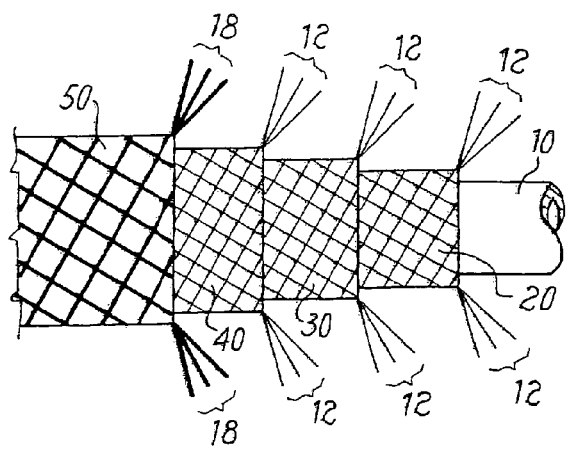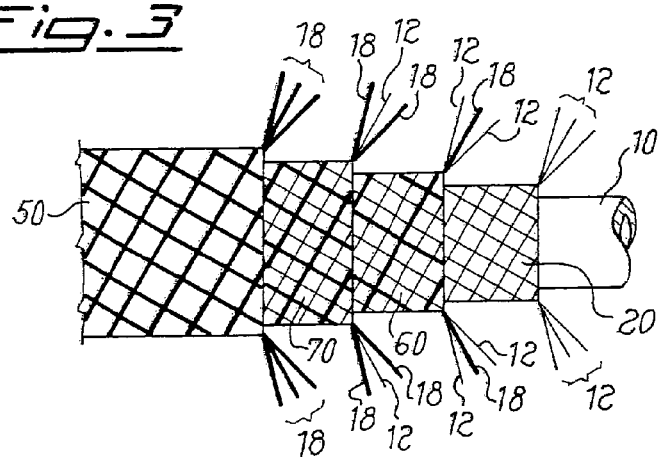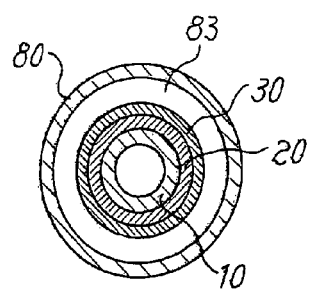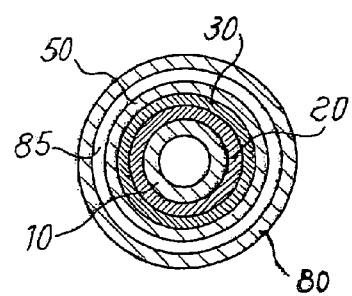

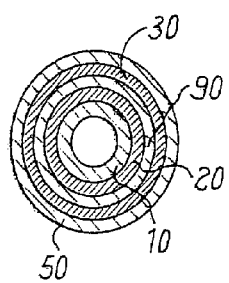
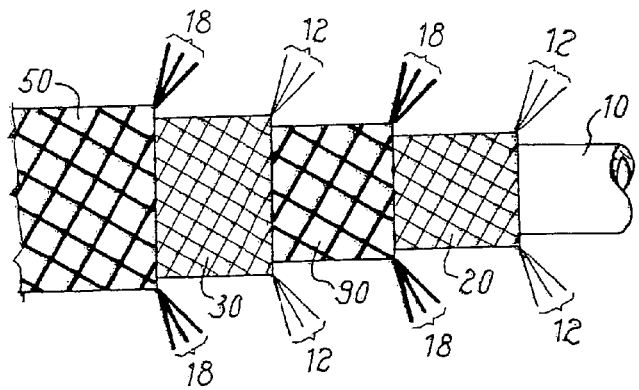
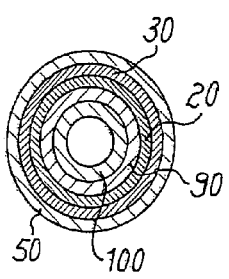
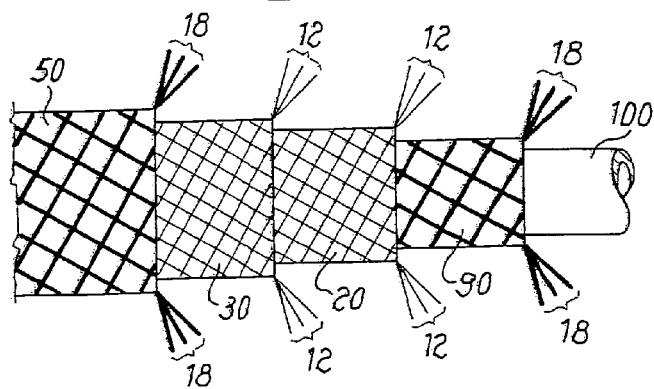
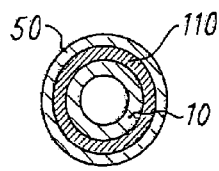
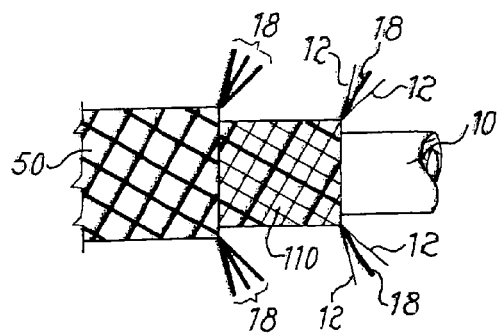

CHROMATOGRAPHY COLUMN ASSEMBLY

This application is the U.S. National Phase of International Application PCT/IB2003/004904, filed 22 Oct. 2003, which designated the U.S. PCT/IB2003/004904 claims priority to Italian Application No. MI 2002A 002310 filed 30 Oct. 2002. The entire content of these applications are incorporated herein by reference.

FIELD OF THE INVENTION

The present invention relates to chromatography column and, in particular a chromatography column assembly of the direct heating type.

BACKGROUND OF THE INVENTION

In the prior art various examples of Chromatography columns are known to be designed for direct heating by means of conductive elements to which electrical power is applied in a controlled way in the attempt to obtain the desired temperatures.

U.S. Pat. No. 5,611,846 by Overton et al. describes a chromatography column assembly with direct heating. This document suggests inserting the capillary column and a conductive filament into an insulating sheath. In practice this solution is subject to phenomena of dispersion and has limits both as regards the maximum length of the column (2-3 meters at the most) and as regards the maximum temperature that can be reached (250° C. at the most).

Another example is constituted by the column assembly described in U.S. Pat. No. 5,808,178 in the name of Thermedics. Among the various embodiments illustrated, it suggests inserting a capillary column made of fused silica into a steel tube. The tube is then coated with an insulating sheath made of woven glass fibers. However this embodiment requires high electrical powers (up to 2 kW) to be applied to the steel tube in order to heat the column. This also makes the position of the column inside the tube difficult to reproduce and makes the temperatures dependent on the distance between the column and the wall of the steel tube.

U.S. Pat. No. 6,217,829 by Mustacich et al. describes a column assembly with heating wires and sensors which to overcome the limits of the Overton solution, are wound tightly in a spiral forming a kind of toroidal shaped pack insulated towards the outside. Due to the casual arrangement of the heating wires in the packing, excessive heatings may occur in specific points of the column, just as in other points the temperature may be lower than that desired. In the same way, temperature detection along the entire column is influenced by the casual distribution of the conductive filaments foreseen for this purpose. This technology is complex and costly to produce. Moreover, the non-uniformity of thermal dispersions between the "core" and the outer surface of the assembly may cause non-uniformity of the temperature in the section of the toroid. Another example of a known type of column assembly is described in the international patent application n. WO 02/40988 in the name of the Applicant.

The column assembly described in this prior art document comprises a capillary column and a single element in an electrically conductive material placed in contact with it. The electrically conductive element is constituted in particular by a plurality of filaments in electrically conductive materials that are woven together to form a tubular mesh that envelops the capillary column. The conductive element produced in this way, which may have filaments in different electrically conductive materials, is used both to heat the column, supplying electrical power to its ends, and to detect the instantaneous temperature of the column by measuring an electrical quantity at its ends.

The assembly constituted by the column and by the electrically conductive tubular mesh is then covered with an outermost tubular mesh, produced by weaving together filaments in electrically insulating material.

From the theoretical point of view, this solution offers considerable advantages compared to the direct heating systems mentioned above, but may not be very versatile from a practical point of view. In fact, it is often necessary to obtain columns of pre-established length with conductive elements having specific electrical properties, for example overall resistance, specific linear resistance and the like. For example, the resistance range of the conductive elements of the column must be established according to the control system. This means that it is necessary to appropriately choose the conductive material to be used, or the diameter of the filaments to be woven to obtain the desired conductive element associated with the column of pre-established length.

Nonetheless, the need to obtain these specific electrical characteristics or properties may also require the use of filaments produced with conductive materials that are not easily workable, or the use of conductive filaments whose diameter is not particularly suitable to be woven or not particularly suitable to provide the finished product with specific dimensions and/or mechanical resistance.

SUMMARY OF THE INVENTION

The task of the present invention is therefore to provide a chromatography column assembly and in particular a column assembly of the direct heating type, which allows the drawbacks of prior art to be overcome.

Within the scope of this task, an object of the present invention is to propose a column assembly of the direct heating type that can be adapted to a wide range of needs with regard to the electrical properties and characteristics of the electrically conductive elements associated with the column.

Another object of the present invention is to propose a column assembly of the direct heating type that can be easily adapted to satisfy particular requirements with regard to the characteristics of workability, production economy, dimensions, mechanical resistance, flexibility and the like.

A further object of the present invention is to propose a column assembly of the direct heating type that may be used with different temperature control systems.

These objects are attained by the present invention, which relates to a chromatography column assembly, of the type comprising at least a capillary column and at least a tubular structure which envelops the capillary column and is coaxial with it, the tubular structure comprising means to directly heat the column, means to detect the temperature of the column and one or more electrically insulating covering elements, characterized in that the tubular structure comprises a plurality of tubular meshes each formed of a plurality of filaments woven together.

The possibility of using several coaxial tubular meshes facilitates the production of column assemblies according to the present invention, for example as regards the type of material with which the electrically conductive filaments are produced and/or their diameter.

According to an advantageous aspect of the present invention, one or more conductive meshes may be produced by weaving together electrically conductive filaments and electrically insulating filaments. This offers the advantage of allowing column assemblies with the desired characteristics of dimensions and mechanical resistance to be produced with the same technique.

The covering elements in electrically insulating material may also be produced with the same technique, that is in tubular form with filaments in electrically insulating material woven together, or may be formed of continuous sheaths in materials with the suitable characteristics of electrical insulation and resistance to high temperatures.

According to needs, the insulating covering elements may form the outermost tubular mesh of the plurality of coaxial tubular meshes, or at least one of the covering elements in electrically insulating material may be interposed between at least two electrically conductive coaxial tubular meshes. In this case it is possible to obtain particular configurations, for example column assemblies in which the heating conductive means may be separate from the conductive means destined to detect the temperature.

In the case in which the capillary column is produced in electrically conductive material, such as metal or the like, one or more insulating covering elements may be interposed between the capillary column and the remaining electrically conductive coaxial tubular meshes.

In general, the chromatography column assembly according to the present invention offers great flexibility as it allows in any case the desired electrical characteristics to be obtained always using conductive filaments made of the same material and with the same diameter. The production technology is thus further simplified, with considerable advantages also in regards to production costs.

Another aspect of the present invention provides a method to produce a chromatography column assembly of the direct heating type. For a certain length L of the capillary column, the resistance R1 of the heating means of the column and/or the resistance R2 of the means to detect the temperature of the column are determined by weaving together a pre-established number of filaments in electrically conductive material to form one or more electrically conductive tubular meshes coaxial with the column. Once the length L of the capillary column has been established, it is possible to set the resistance most suitable for the function performed by each of the electrically conductive means, for example by producing several tubular conductive meshes in contact with one another by means of conductive filaments of the same material and of the same diameter.

To obtain the desired values of electrical resistance of each conductive means, one or more meshes may be produced by weaving together mixed filaments, that is electrically conductive filaments and electrically insulating filaments.

Advantageously, this makes it possible to use conductive filaments of the same material and of the same diameter for all the tubular meshes, thus offering, as well as greater production flexibility, also the aforesaid advantages of simplicity and economy in the production phase.

Naturally, it would also be possible to produce any of the tubular meshes by weaving together conductive and/or insulating filaments of different diameters. In the same way, each mesh may be produced with filaments having a diameter different from the diameter of the filaments of any other mesh.

BRIEF DESCRIPTION OF THE DRAWINGS

Further characteristics and advantages of the present invention shall become apparent from the description hereunder with reference to the accompanying schematic drawings, in which:

FIG. 1 is a sectional view of a possible embodiment of the column assembly according to the present invention;

FIG. 2 shows the composition of the column assembly in FIG. 1;

FIG. 3 shows the composition of a column assembly according to another possible embodiment of the present invention;

FIGS. 4 and 5 are cross sectional views of other embodiments of a column assembly according to the present invention;

FIG. 6 is a sectional view of another embodiment of the column assembly according to the present invention;

FIG. 7 shows the composition of the column assembly in FIG. 6;

FIG. 8 is a sectional view of yet another embodiment of the column assembly according to the present invention;

FIG. 9 shows the composition of the column assembly in FIG. 8;

FIG. 10 is a sectional view of an alternative embodiment of the column assembly according to the present invention; and FIG. 11 shows the composition of the column assembly in FIG. 10.

DETAILED DESCRIPTION OF ILLUSTRATED EMBODIMENTS

In the illustrations described schematically hereunder, the electrically conductive meshes are represented in section with a dashed line that is thicker than the one representing the insulating covering elements, while in the views illustrating the compositions of the column assemblies the filaments in electrically conductive material are represented with a dashed line that is thinner than the one representing the filaments in electrically insulating material. The column assembly represented in FIGS. 1 and 2 comprises a capillary column 10, produced for example in fused silica or another electrically insulating material, on which is woven a plurality of electrically conductive coaxial tubular meshes 20, 30 and 40, each formed of a plurality of filaments woven together. On the outside, the assembly thus formed is provided with an electrically insulating covering element 50, also tubular in shape and coaxial with the column 10 and with the electrically conductive tubular meshes 20, 30 and 40.

In this embodiment, all the electrically conductive tubular meshes 20, 30 and 40 are produced by weaving together filaments 12 in electrically conductive material, for example nickel and its alloys, or any other metallic or non-metallic electrically conductive material, suitable to be woven to form a tubular mesh.

The tubular meshes 20, 30 and 40 are preferably placed in close contact with one another and, in particular the innermost tubular mesh is preferably placed in close contact with the outer surface of the column 10, although without being integral with each other. This allows absorption of the various thermal deformations to which the tubular meshes are subject in relation to the column, while making heat exchange between the electrically conductive elements 20, 30, 40 and the column more efficient and rapid.

The electrically insulating covering element 50 is represented here as a tubular mesh placed in close contact with the conductive tubular meshes 20, 30 and 40 and obtained by weaving together filaments 18 in electrically insulating material, for example ceramic fibers, glass fibers, or other electrically insulating materials particularly resistant to heat and suitable to be woven to form a tubular mesh. Alternatively, the electrically insulating covering element 50 may also be constituted by a tubular insulating sheath, for example made of polyamide or the like.

FIG. 3 shows a column assembly in which some of the conductive tubular meshes are produced by weaving together mixed filaments, some electrically conductive and others electrically insulating. In fact, besides the tubular mesh 20, produced entirely with filaments 12 in electrically conductive material, in this case two tubular meshes 60 and 70 are also provided, produced by weaving together electrically conductive filaments 12 and electrically insulating filaments 18.

The number, composition and arrangement of the electrically conductive tubular meshes 20, 60 and 70 may in any case vary in respect of those illustrated. For example, the tubular mesh 20 could also be produced with mixed filaments and all the meshes could have the same composition of conductive and insulating filaments. The covering element 50 in electrically insulating material in this case is also illustrated in the form of a tubular mesh formed of filaments 18 in electrically insulating material, although it can also be made in this case of a tubular sheath.

For example, in the section shown in FIG. 4, the column assembly formed of the column 10 and of two electrically conductive tubular meshes 20 and 30, is enclosed in an electrically insulating covering 80 with a slightly larger diameter than the external diameter of the tubular mesh 30. This makes it possible to form a cavity 83 in which a heat-exchange fluid may circulated. In this case the tubular covering 80 is preferably formed of a continuous tubular film waterproof to the circulating fluid rather than of a tubular mesh, or may also be a tubular mesh, in turn covered with a waterproofing material.

In the sectional view in FIG. 5, the same column assembly of FIG. 4 also includes an electrically insulating covering 50, produced in the form of tubular mesh, placed in close contact with the outermost conductive tubular mesh 30. Between the external sheath 80 and the insulating covering 50 there is once again a cavity 85 for circulation of a heat-exchange fluid.

An electrically insulating tubular element 50 or 80, which envelops the outermost conductive mesh, allows, according to custom, the column assembly to be wound in coils without giving rise to short circuits or unwanted electrical contacts between the conductive elements of the column assembly.

In the embodiments illustrated above, with reference to FIGS. 1 to 5, the electrically conductive tubular meshes are used both as means to directly heat the column 10 and as means to detect the temperature of the column.

Alternatively, one or more of the conductive tubular meshes may be used for direct heating of the column, while one or more of the others may be used to detect the temperature of the column. This allows conductive materials that guarantee optimal characteristics to be chosen both for the heating element and for the temperature sensor.

An example of a column assembly produced in this way is shown in FIGS. 6 and 7, wherein the column 10 is surrounded by a first electrically conductive mesh 20 and is separated from another electrically conductive mesh 30 by a tubular mesh 90 produced with electrically insulating materials. The two conductive elements 20 and 30 are thus electrically insulated from each other and may be used independently to heat the column or to detect the temperature. Naturally, the number of tubular meshes may also be greater in respect of the number shown and two or more meshes may be also be used for each function. The insulating mesh 90 too may be covered by an electrically insulating material to improve the electrical insulation between the separated conductive elements.

FIGS. 8 and 9 show a column assembly in which the capillary column 100 is produced in electrically conductive material, such as a metal or the like. In this case, the column 100 is electrically insulated in respect of the conductive meshes 20 and 30 by interposing a mesh 90 in electrically insulating material.

The tubular meshes may be used both to heat the column 100 directly and to detect the temperature. Nonetheless, the electrical conductivity of the column 100 could also be used to produce one of the two functions (heating or detecting the temperature of the column), while the other function could be performed by the tubular meshes 20 and 30.

FIGS. 10 and 11 show an alternative embodiment that makes it possible to obtain the objects of the present invention. The column assembly represented here comprises a single electrically conductive tubular mesh 110 formed of a mesh of filaments 12 in electrically conductive material and of filaments 18 in electrically insulating material. In fact, to obtain specific resistance characteristics of the conductive element, it may be necessary to use a quantity of conductive filaments 12 whose number does not allow the formation of a tubular mesh suitable to be woven on the column 10. In this case, filaments 18 in electrically insulating material are used to form an adequate conductive mesh that not only has the desired electrical characteristics but also the desired mechanical properties of the mesh.

Various modifications may be made without departing from the scope of the present invention, For example, each of the conductive and/or insulating tubular meshes may be produced both with filaments of identical diameter and with filaments with different diameters, and each mesh may be produced with filaments with a diameter different from the diameter of the filaments of any other mesh. Moreover, each of the conductive meshes may be produced with mixed electrically conductive filaments, that is filaments that may be made of different materials or with filaments made of the same electrically conductive material but with different resistivity characteristics.

The invention claimed is:

1. A chromatography column assembly, of the type comprising at least one capillary column, at least one tubular structure which envelops said capillary column and is coaxial with it, means to directly heat said column, means to detect the temperature of said column and one or more electrically insulating covering elements, wherein said tubular structure comprises a plurality of tubular meshes each formed of a plurality of filaments woven together, wherein said means to heat said column and/or said means to detect the temperature of said column comprise at least one electrically conductive tubular mesh formed at least in part of filaments in electrically conductive material and at least in part of filaments in electrically insulating material woven together.

2. A chromatography column assembly as claimed in claim 1, wherein at least one of said one or more electrically insulating covering elements comprise at least one tubular mesh formed of filaments in electrically insulating material woven together.

3. A chromatography column assembly as claimed in claim 1, wherein the innermost mesh of said plurality of coaxial tubular meshes has an inner surface placed in close contact with the outer surface of said column.

4. A chromatography column assembly as claimed in claim 1, wherein at least one of said electrically insulating covering elements constitutes the outermost tubular mesh of said plurality of coaxial tubular meshes.

5. A chromatography column assembly as claimed in claim 1, wherein at least one of said electrically insulating covering elements constitutes the innermost tubular mesh of said plurality of coaxial tubular meshes.

6. A chromatography column assembly as claimed in claim 1, wherein at least one of said electrically insulating covering elements is interposed between at least two coaxial tubular meshes of said plurality of coaxial tubular meshes.

7. A chromatography column assembly as claimed in claim 1, wherein said capillary column is produced in fused silica or another suitable electrically insulating material.

8. A chromatography column assembly as claimed in claim 1, wherein said capillary column is produced in an electrically conductive material, such as a metal or the like.

9. A chromatography column assembly as claimed in claim 8, wherein said means to heat said column and/or said means to detect the temperature of said column are constituted by said capillary column in electrically conductive material.

10. A chromatography column assembly as claimed in claim 1, wherein said means to heat said column comprise at least one first of said electrically conductive coaxial tubular meshes and said means to detect the temperature of said column comprise at least one second of said electrically conductive coaxial tubular meshes, at least one covering element in electrically insulating material being interposed between said first and said second tubular mesh.

11. A method to produce a chromatography column assembly of the direct heating type, wherein said chromatography column assembly comprises at least one capillary column, one or more electrical conductors to directly heat said column and one or more electrical conductors to detect the temperature of said column, comprising:

establishing a predetermined length L for said capillary column; and for said predetermined length L of said column, determining at least a resistance R1 of said one or more electrical conductors to heat said column by weaving together a pre-established number of filaments in electrically conductive material to form one or more electrically conductive tubular meshes coaxial with said column.

12. A method as claimed in claim 11, wherein one or more meshes of said one or more electrical conductors comprise filaments in electrically insulating material woven with said filaments in electrically conductive material.

13. A method as claimed in claim 11, wherein said one or more electrical conductors to heat said column coincide with said one or more electrical conductors to detect the temperature of said column.

14. A method as claimed in claim 11, wherein said electrically conductive filaments are produced with the same material.

15. A method as claimed in claim 11, wherein said electrically conductive filaments that form at least one of said one or more meshes all have the same diameter.

16. A method as claimed in claim 11, wherein said electrically conductive filaments that form said one or more meshes all have the same diameter.

17. A method to produce a chromatography column assembly of the type with direct heating, wherein said chromatography column assembly comprises at least one capillary column, one or more electrical conductors to directly heat said column and one or more electrical conductors to detect the temperature of said column, comprising:

establishing a predetermined length L for said capillary column; and for said predetermined length L of said column, determining at least a resistance R2 of said one or more electrical conductors to detect the temperature of said column by weaving together a pre-established number of filaments in electrically conductive material to form one or more electrically conductive tubular meshes coaxial with said column.

18. A method as claimed in claim 17, wherein one or more meshes of said one or more electrical conductors comprise filaments in electrically insulating material woven with said filaments in electrically conductive material.

19. A method as claimed in claim 17, wherein said one or more electrical conductors to heat said column coincide with said one or more electrical conductors to detect the temperature of said column.

20. A method as claimed in claim 17, wherein said electrically conductive filaments are produced with the same material.

21. A method as claimed in claim 17, wherein said electrically conductive filaments that form at least one of said one or more meshes all have the same diameter.

22. A method as claimed in claim 17, wherein said electrically conductive filaments that form said one or more meshes all have the same diameter.

* * * * *